US006753020B1

(12) United States Patent
Mayne

(10) Patent No.: US 6,753,020 B1
(45) Date of Patent: Jun. 22, 2004

(54) COMPOSITION CONTAINING OAT EXTRACT FOR INCREASED CELL RENEWAL RATE

(75) Inventor: James R. Mayne, Kentwood, MI (US)

(73) Assignee: Alticor Inc., ADA, MI (US)

(*) Notice: Subject to any disclaimer, the term of this patent is extended or adjusted under 35 U.S.C. 154(b) by 235 days.

(21) Appl. No.: 09/684,826

(22) Filed: Oct. 10, 2000

(51) Int. Cl.⁷ ................................................ A61K 7/48

(52) U.S. Cl. ........................ 424/750; 424/401; 514/944

(58) Field of Search ................................ 424/401, 725, 424/750; 514/944

(56) References Cited

U.S. PATENT DOCUMENTS

| | | | |
|---|---|---|---|
| 4,014,995 A | | 3/1977 | Juliano et al. |
| 4,238,509 A | | 12/1980 | Evans et al. |
| 4,363,815 A | | 12/1982 | Yu et al. |
| 4,548,728 A | | 10/1985 | Franklin |
| 4,883,659 A | | 11/1989 | Goodman et al. |
| 4,886,665 A | | 12/1989 | Kovacs |
| 5,352,389 A | | 10/1994 | Gazzani |
| 5,441,740 A | | 8/1995 | Ozlen |
| 5,449,519 A | | 9/1995 | Wolf et al. |
| 5,468,491 A | | 11/1995 | Targan |
| 5,470,874 A | | 11/1995 | Lerner |
| 5,573,785 A | | 11/1996 | Murphy |
| 5,888,521 A | | 3/1999 | Zimmerman |
| 6,074,647 A | * | 6/2000 | Zimmerman et al. |
| 6,184,247 B1 | * | 2/2001 | Schneider |

FOREIGN PATENT DOCUMENTS

| | | |
|---|---|---|
| DE | 195 15 609 C1 | 4/1996 |
| EP | 0 676 194 A | 10/1995 |
| EP | 0 739 621 A1 | 10/1996 |
| EP | 0 894 494 A | 2/1999 |
| FR | 2 597 337 | 10/1987 |
| FR | 2 720 643 | 8/1995 |
| GB | 1 468 295 A | 3/1977 |
| GB | 2 328 374 A | 2/1999 |
| JP | 55-164613 A * | 12/1980 |
| WO | WO 00 04867 A | 2/2000 |

OTHER PUBLICATIONS

Chemical Abstract No. 531391, EMBASE No. 76115593, *Therapeutic Use of 'AVENA' Skin Cleansing Preparations*, Kuerner H. Karlstr. 29, Karlsruhe Germany West; Z. Hautkr. (Germany, West), 1975, 50/15 (631–635).
Chemical Abstract, No 12064007, PASCAL No. 95–0263947; *Oats: Chemistry. Technology and Potential Uses in the Cosmetic Industry*; Paton, D.; Bresciani, S.; Nam Fong Han; Hart, J.; Journal: Cosmetics and Toiletries; 1995, 110(3) 63–70 (5 p.).

Chemical Abstract, No. 00911864, PASCAL No. 76–0006664; *Therapeutischer erfahrungsbericht mit der avena–reihe (Resultats therapeutiques obtenus avec les produits avena)*; Kurner H. Ankermann & Co. G.M.B.H., Friesoythe, Journal: Z. Hautkrankh, 1975, 50 (15) 631–635.
Chemical Abstract, No. 001371746; WPI Acc No. 75–21383W/13; Patent Assignee: Quaker Oats Co.; Priority Data (CC No. Date): US 398651 (730919); US 565695 (750407).
Chemical Abstract, No. 010545082; WPI Acc No. 96–042035/05; Patent Assignee: Clarins; Priority Data (CC No. Date); FR 946837 (940603).
Chemical Abstract, No. 010338357; WPI Acc. No. 95–240445/31; Patent Assignee: Nurture Inc; Priority Data (CC No Date); US 172485 (931223).
Chemical Abstract, No. 010002632; WPI Acc. No. 94–270343/33; Patent Assignee: (Kono) Konovalov II; Priority Data (CC No Date); SU 5016466 (911228).
Chemical Abstract, No. 009708838; WPI Acc. No. 93–402391/50; Patent Assignee: (AERO=) Aerozol sci prodn assoc; (stal=) stalgen agric firm; Priority Data (CC No Data); SU 4868052 (900921).
Chemical Abstract, No. 00362016; Derwent Accession No.: 73–35329; *A New Natural Ingredient for Cosmetic Formulators*; Assignee: Quaker–Oats (Cleveland Ohio USA); Journal: Drug Cosmet. Ind., 113, No. 3, 48, 50, 52, 54, 56, 1973.
Chemical Abstract, No. 124298400; CA: 124 (22)298400u; *Formulating personal care products with hydrolyzed oat protein*; Author(s): Longcar, Clifford; Journal: Household Pers. Prod. Ind.; Date: 1996, vol.: 33; No.: 3; pp. 85–87.
Chemical Abstract, No. 124269972; CA: 124(20)269972(b); *Hair and Scalp Conditioners Containing Oat Extract and Hydroxy Acids*, Inventor (Author) Onitsuka, Satoshi; Dubowoj, Polina; Assignee: Kao Corporation GMBH; Patent: Germany; DE 19515609 C1; Date: Mar. 28, 1996.
Chemical Abstract, No. 123152610; CA: 123(12)152610v; *Oat Oil Compositions with Useful Dermatological Properties*; Inventor (Author); Potter, Richard; Castro, James M.; Moffatt, Lori C.; Assignee: Nurture, Inc., Patent: PCT International; WO 9517162 A1; Date: Jun. 29, 1995; pp. 36 pp.
Chemical Abstract, No. 94109095; CA: 94(14)109095b; *The Water Oat Extracts as Skin Cosmetics*; Assignee: Onodera, Hiroshi; Patent: Japan Kokai Tokkyo Koho JP 80164613; Date: Dec. 22, 1980.

(List continued on next page.)

Primary Examiner—Jyothsna Venkat
(74) Attorney, Agent, or Firm—Brinks Hofer Gilson & Lione; G. Peter Nichols

(57) ABSTRACT

The present invention relates to a method of enhancing the rate of skin desquamation by incorporating an oat extract into a cosmetic composition suitable for application to mammalian skin. The composition is preferably free of known skin exfoliation agents.

11 Claims, No Drawings

OTHER PUBLICATIONS

Chemical Abstract, No. 88197417; CA: 88(26)197417n; *Cosmetic Ingredients*; Author(s): Miller, Aaron; Location: Kalar Lab., Chicago, Ill.; Journal: Soaps, Deterg. Toiletries Rev., Date: 1977; vol.: 7; No.: 9; pp. 21–25.

Chemical Abstract, No. 80030602; CA: 80(6)30602s; *New Natural Ingredient for Cosmetic Formulators*; Author(s): Coe, John; Juliano, Angelo; Journal: Drug Cosmet. Ind.; Date: 1973; vol.: 113; No.: 3; pp.: 48, 50, 52, 54, 56.

Chemical Abstract, No. 0458058; *This Cosmetic Company Really Knows its Oats*, Business Week, Feb. 22, 1993; p. 91; No. 3306.

Chemical Abstract, No. 0083399002; WPI Acc No: 90–286003/38; *Cosmetic Acerola extract—obtd. by washing with water, removing ppte. decolouring and filtering*; Patent Assignee: (NICH–) Nichirei KK; Priority Data (CC No. Date): JP 8916185 (Jan. 27, 1989).

Chemical Abstract, No. 007353231; WPI Acc No.: 87–3502237/50; *Two–part skin anti–ageing cosmetic compsn.—contg, active principle hidering skin ageing due to formation and action of free radicals*; Patent Assignee: (Cour) Courtin O; (Clar–) Clarins; Priority Data: (CC No Date): FR 8788 (870000); FR 8416038 (Oct. 19, 1984).

Chemical Abstract, No. 108226675; CA: 108(26)226675j; *Cosmetic containing antioxidants to delay the aging of skin*; Application: FR 8788 (Jan. 7, 1987).

*Oats; Chemistry, Technology and Potential Uses in the Cosmetic Industry, High purity oat derivatives show potential as plant–based conditioning ingredients for skin–and hair–care*; David Paton and Sandra Bresciani; Agriculture and Agri–Food Canada, Saskatoon, SK, Canada; Nam Fong Han, Canamino, Inc., Ottawa, ON, Canada; Janice Hart. Canamino Inc., Long Island, NY, USA; Cosmetics & Toiletries Magazine, vol. 110, Mar. 1995, pp. 63–70.

Photocopy of front and back of product container, Vaseline® Brand Intensive Care® Lotion.

*Hydroxy Acids and Skin Aging* by Walter P. Smith, Walter Smith Consultants, Soap Cosmetics Chemical Specialties, Sep. 1993, vol. 69, No. 9, pp. 54–58 and 76.

* cited by examiner

COMPOSITION CONTAINING OAT EXTRACT FOR INCREASED CELL RENEWAL RATE

BACKGROUND OF THE INVENTION

The present invention relates to a composition to enhance the rate of skin cell renewal or exfoliation and to a method of increasing the skin cell renewal rate without an increase in skin irritation. In particular, the present invention relates to a composition containing a skin benefit agent that includes oat extract. The present invention also relates to a method of increasing the rate of skin-cell renewal by applying a composition to the skin, wherein the composition comprises an amount of oat extract effective to increase skin cell turnover or renewal rate.

The skin of humans is continually assaulted by environmental conditions such as the sun, wind, and pollution. These environmental assaults weather or age the skin causing, among other things, wrinkles, age spots and other undesirable skin conditions. In addition, the effects of natural aging also cause the skin to wrinkle.

These negative effects can be prevented or at least ameliorated by applying skin care cosmetics that contain skin benefit agents according to the present invention.

Human skin may be classified into two major parts: the outer layer or epidermis and an underlying layer or dermis. The dermis contains among other things, blood vessels, nerves, collagen, elastin, and fibroblast cells, which are responsible for the biosynthesis of collagen and elastin.

The epidermis itself also may be considered to consist of two major zones, an inner or malpighian layer and an outer or horny layer. The malpighian layer, a living tissue, may be further divided into basal, spinous, and granular layers. The horny layer, a dead tissue, is also referred to as stratum corneum.

In the natural process, basal cells in the basal layer move outward through the spinous and granular layers to become dead cells called corneocytes, in the stratum corneum. The stratum corneum consists of approximately 14 layers of corneocytes. In the normal skin it takes about 14 days for the basal cells to move from the basal layer to the end of the granular layer and to become corneocytes, and another 14 days to reach the outermost layer of the stratum corneum, where they are naturally shed or exfoliated. This process of forming corneocytes is called keratinization, and stratum corneum is the natural products produced by this process. The stratum corneum is the skin tissue that one feels when touching the skin. Usually, it takes about 28 days for cells of the basal layer to move outward to the surface in the course of making new skin.

It is thought that by increasing the natural desquamation rate (the cell renewal or cell turnover rate) of the outermost part of the stratum corneum and thus exposing lower layers of the stratum corneum, the appearance of the skin will be improved. Many substances are known to increase the rate of natural desquamation but recently compositions containing hydroxycarboxylic (alpha and beta) acids have received an increasing amount of attention.

A drawback to the use of hydroxycarboxylic acids is that they are most effective at low pHs, about 4.0 or less. It appears, however, that there exists a strong correlation between the degree of exfoliation (cell renewal rate) and the degree of irritation. Thus, at pH of about 4.0 or less, the hydroxycarboxylic acids show significant stimulation of cell renewal but also a fair degree of skin irritation. On the other hand, as the pH approaches neutral (7.0), the cell renewal rate decreases while there is little or no irritation. Thus, it would be desirable to achieve an increase in the rate of natural desquamation without further increasing the irritation of the skin. It would be most desirable to provide for enhanced skin desquamation at a neutral pH. The present invention solves that problem by providing for enhanced skin desquamation at a neutral pH without undue irritation.

One method for ameliorating the irritating effects of the alpha-hydroxy acids is described in GB 2,328,374. There, a complex of oat protein and malic acid is provided where the malic acid is chemically bonded or complexed with hydrolyzed oat protein.

Another method is disclosed in U.S. Pat. No. 5,888,521. There, the composition contains an alpha-hydroxy acid and an oat extract that contains less than 1% β-glucan. It is noted that the oat extract synergistically enhances the rate of skin desquamation produced by the hydroxy acid.

None of this art, however, teaches or recognizes that an oat extract, by itself, is effective in enhancing mammalian skin cell renewal rate at near neutral pH, without undue skin irritation.

SUMMARY OF THE INVENTION

In accordance with the present invention, there is provided a cosmetic or dermopharmaceutical composition for topical use comprising an oat extract and a carrier. In accordance with this aspect of the present invention, there is provided a composition comprising an oat extract present in a therapeutically effective amount in a topically acceptable vehicle for application to human skin to enhance the rate of skin desquamation beyond the rate of naturally occurring skin desquamation. In other words, this aspect contemplates the use of an oat extract in the preparation of a cosmetic composition to enhance the rate of skin desquamation beyond the rate of naturally occurring skin desquamation.

Advantageously, compositions of the present invention need not contain known skin desquamation agents such as hydroxy acids to achieve enhanced skin desquamation rates. Therefore, in one aspect of the present invention, the compositions may be substantially free or completely free of known skin desquamation (exfoliation) agents such as hydroxy acids. The term "substantially free" is used to mean that the compositions contain less than about 0.1% known skin desquamation agents such as hydroxy acids.

The oat extract is derived from oat, avena sativa. Preferably, the oat extract is a hydroglycolic extract, is soluble, and does not contain β-glucan. In other words, the oat extract does not contain a measurable amount of β-glucan, e.g., less than about 0.01%. The oat extract may be incorporated into a solvent for ease of handling. For example, in a preferred embodiment, the oat extract is incorporated in a 1:1 v/v mixture of 1,3 butylene glycol and water.

In one embodiment, the oat extract contains from about 10% to about 90% carbohydrate and from about 10% to about 90% protein.

Generally, the composition contains from about 0.01 to about 99 percent by weight of the total composition. Preferably, the concentration of oat extract ranges from about 0.05% to about 30%, more preferably from about 0.1% to about 15%.

Preferably, the composition has a pH in the range from about 5.0 to about 9.0, preferably from about 6.0 to about 8.0.

Another aspect of the present invention includes a method of increasing the rate of skin exfoliation or desquamation comprising topically applying a cosmetic composition containing an amount of an oat extract effective to enhance the rate of skin cell desquamation beyond the naturally occurring rate of skin cell desquamation. In this aspect, the method includes topically applying to the skin a composition comprising an oat extract in an amount and for a period of time sufficient to increase the rate of natural skin desquamation.

DETAILED DESCRIPTION OF THE INVENTION

In accordance with the present invention, a composition acceptable for topical application to the skin comprises an oat extract and a carrier. Compositions of the present invention need not contain known skin desquamation agents such as hydroxy acids to achieve enhanced skin desquamation rates. Therefore, in one aspect of the present invention, the compositions may be substantially free or completely free of known skin desquamation (exfoliation) agents such as hydroxy acids.

The oat extract useful in the present invention is derived from oat, avena sativa. Preferably, the oat extract is a hydroglycolic extract, is soluble, and does not contain β-glucan. In other words, the oat extract does not contain a measurable amount of β-glucan, e.g., less than about 0.01%. The oat extract may be incorporated into a solvent for ease of handling. For example, in a preferred embodiment, the oat extract is incorporated in a 1:1 v/v mixture of 1,3 butylene glycol and water.

Sources of suitable oat extract have been obtained from Canamino Inc. under their trade name Ostar™ Arriveen BG, from Brooks, Vegi-Tech, and Croda.

In one embodiment, the oat extract contains from about 10% to about 90% carbohydrate and from about 10% to about 90% protein.

To prepare the compositions according to the present invention, the oat extract is mixed with a pharmaceutically or cosmetically acceptable vehicle or carrier.

The compositions of the present invention may be formulated as a solution, gel, lotion, cream, ointment, oil-in-water emulsion, water-in-oil emulsion, or other pharmaceutically acceptable form. The compositions of the present invention may also contain various known and conventional cosmetic ingredients so long as they do not detrimentally affect the desired enhancement of skin desquamation.

The cosmetically acceptable vehicle acts as a dilutant, dispersant or carrier for other materials present in the composition, so as to facilitate their distribution when the composition is applied to the skin.

Vehicles other than water can include liquid or solid emollients, solvents, humectants, thickeners and powders. As used herein, "emollients" refer to materials used for the prevention or relief of dryness, as well as for the protection of the skin. A wide variety of suitable emollients are known and may be used herein. Sagarin, *Cosmetics, Science and Technology*, 2nd Edition, Vol. 1, pp. 32–43 (1972), incorporated herein by reference, contains numerous examples of suitable materials.

Vehicles may also include propellants such as propane, isobutane, dimethyl ether, carbon dioxide, nitrous oxide; and solvents such as ethyl alcohol, isopropanol, acetone, ethylene glycol monomethyl ether, diethylene glycol monobutyl ether, diethylene glycol monoethyl ether, or powders such as chalk, talc, fullers earth, kaolin, starch, gums, collodial silica, sodium polyacrylate, tetra alkyl and/or trialkyl aryl ammonium smectites, chemically modified magnesium aluminum silicate, organically modified montmorillonite clay, hydrated aluminum silicate, fumed silica, carboxyvinyl polymer, sodium carboxymethyl cellulose, ethylene glycol monostearate.

The composition can optionally comprise suncreens such as inorganic and organic sunscreens to provide protection from the harmful effects of excessive exposure to sunlight during use of the composition of the present invention.

Examples of suitable organic sunscreens, when required, include those set out in the current OTC Sunscreen Monograph, which is incorporated herein by reference. The composition of the invention can accordingly comprise from 0.1 to 10%, preferably from 1 to 5% by weight of an organic sunscreen material.

The composition optionally can also comprise inorganic sunscreens such as titanium dioxide, zinc oxide, having an average particle size of from 1 to 300 nm, iron oxide, having an average particle size of from 1 to 300 nm, silica, such as fumed silica, having an average particle size of from 1 to 100 nm. It should be noted that silica, when used as an ingredient in the emulsion according to the invention can provide protection from infrared radiation.

Ultrafine titanium dioxide in either of two forms, namely water-dispersible titanium dioxide and oil-dispersible titanium dioxide may be used. Water-dispersible titanium dioxide is ultrafine titanium dioxide, the particles of which are uncoated or which are coated with a material to impart a hydrophilic surface property to the particles. Examples of such materials include aluminum oxide and aluminum silicate. Oil-dispersible titanium dioxide is ultrafine titanium dioxide, the particles of which exhibit a hydrophobic surface property, and which, for this purpose, can be coated with metal soaps such as aluminum stearate, aluminum laurate or zinc stearate, or with organosilicone compounds.

By "ultrafine titanium dioxide" is meant particles of titanium dioxide having an average particle size of less than 100nm, preferably from 10 to 40nm and most preferably from 15 to 25 nm. The total amount of titanium dioxide that can optionally can be incorporated in the composition according to the invention is from 1 to 25%, preferably from 2 to 10% and ideally from 3 to 7% by weight of the composition.

Optional Skin Benefit Materials and Cosmetic Adjuncts

A particularly convenient form of the composition is an emulsion, in which case an oil or oily material (emollient) will normally be present, together with an emulsifier to provide either a water-in-oil emulsion or an oil-in-water emulsion.

The composition can also comprise water, usually up to 95%, preferably from 5 to 95% by weight.

Silicone Surfactant

The composition can also optionally comprise a high molecular weight silicone surfactant that can also act as an emulsifier, in place of or in addition to the option emulsifier(s) already mentioned.

The silicone surfactant is a high molecular weight polymer of dimethyl polysiloxane with polyoxethylene and/or polyoxpropylene side chains having a molecular weight of from 10,000 to 50,000 and having the structure:

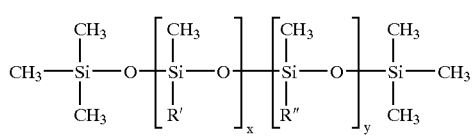

where the groups R' and R" are each chosen from —H, $C_{1-18}$ alkyl and

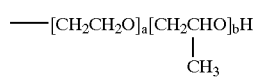

where the groups R' and R" are each chosen from —H, $C_{1-18}$ alkyl and a has a value of from 9 to 115,
b has a value of from 0 to 50,
x has a value of from 133 to 673,
y has a value of from 25 to 0.25.

Preferably, the dimethyl polysiloxane polymer is one in which:

a has a value of from 10 to 114,
b has a value of from 0 to 49,
x has a value of from 388 to 402,
y has a value of from 15 to 0.75. one of groups R' and R" being lauryl, and the other having a molecular weight of from 1000 to 5000.

A particularly preferred dimethyl polysiloxane polymer is one in which:

a has the value 14,
b has the value 13,
has the value 249,
y has the value 1.25.

The dimethyl polysiloxane polymer is conveniently provided as a dispersion in a volatile siloxane, the dispersion comprising, for example, from 1 to 20% by volume of the polymer and from 80 to 99% by volume of the volatile siloxane. Ideally, the dispersion consists of a 10% by volume of the polymer dispersed in the volatile siloxane.

Examples of the volatile siloxanes in which the polysiloxane polymer can be dispersed include polydimethyl siloxane (pentamer and/or hexamer).

A particularly preferred silicone surfactant is cyclomethicone and dimethicone copolyol, such as DC 3225C Formulation Aid available from DOW CORNING. Another is laurylmethicone copolyol, such as DC Q2-5200, also available from Dow Corning.

The amount of silicone surfactant, when present in the composition will normally be up to 25%, preferably from 0.5 to 15% by weight of the emulsion.

Other Cosmetic Adjuncts

Cosmetic adjuncts can form the balance of the composition. Examples of conventional adjuncts which can optionally be employed include preservatives, such as para-hydroxy benzoate esters; antioxidants, such butyl hydroxy toluene; humectants, such as glycerol, ethoxylated glycerins such as glycereth-26, sorbitol, 2-pyrrolidone-5-carboxylate, dibutylphthalate, gelatin, polyethylene glycol, such as PEG 200–600; amino acids such as proline, pyrrolidone carboxylic acid, its derivatives and salts, saccharide isomerate, panthenol, buffers together with a base such as triethanolamine or sodium hydroxide; waxes, such as beeswax, ozokerite wax, paraffin wax; plant extracts, such as Aloe Vera, cornflower, witch hazel, elderflower, cucumber; as well as acerola cherry fermentate, thickeners; activity enhancers; colorants; and perfumes.

Cosmetic adjuncts may also include anti-inflammatory and/or anti-irritant agents. The natural anti-inflammatory and/or anti-irritant agents are preferred. For example, licorice and its extracts, dipotassium glycyrrhizinate, candelilla wax, alpha bisabolol, aloe vera, Manjistha (extracted from plants in the genus Rubia, particularly *Rubia cordifolial*), and Guggal (extracted from plants in the genus Commiphora, particularly *Commiphora Mukul*), may be used.

Additional cosmetic adjuncts may include skin conditioning agents such as hyaluronic acid, its derivatives and salts, including sodium hyaluronate, plant extracts such as kola nut, guarana, mate, algae extract, ceramides, glycoceramides, pseudoceramides, sphingolipids such as sphingomyelins, cerebrosides, sulphatides, and ganglioside, sphingosines, dihydrosphingosine, phytosphingosines, and phospholipids, either separately or in mixtures. Fatty acids may also be combined with these skin benefit agents. For example, the ceramides and glycoceramides include those described in U.S. Pat. No. 5,589,178, 5,661,118, and,5,688,752, the relevant portions of which are incorporated herein by reference. For example, the pseudoceramides include those described in U.S. Pat. No. 5,198,210; 5,206,020; and 5,415,855, the relevant disclosures of which are incorporated herein by reference.

In accordance with one aspect of the present invention, the rate of natural skin desquamation may be increased by topical application to the skin of the compositions according to the present invention. In this regard, the present invention encompasses a method of enhancing the rate of natural skin desquamation comprising topically applying to the skin a composition comprising an oat extract in an amount and for a period of time sufficient to increase the rate of natural skin desquamation. Preferably, the composition is as described above. More preferably, the compositions are substantially free or completely free of known skin desquamation agents.

Generally, the topical application is on at least a daily basis and may be applied for any suitable period of time. Within a few days, a user may notice improvement in skin texture and smoothness.

The following examples illustrate, but do not limit, the present invention. Unless otherwise indicated, all parts and percentages are by weight.

EXAMPLE 1

The following are illustrative examples of formulations and compositions according to this invention. Although the examples use only selected compounds and formulations, it should be understood that the following examples are illustrative and not limited.

The following compositions were prepared to determine their Therapeutic Index (described below). The compositions are suitable for daily application.

TABLE 1

| INGREDIENT | Formula A (wt. %) | Formula B (wt %) |
|---|---|---|
| Water | 93.75 | 88.75 |
| Oat Extract | 5.00 | 10.00 |
| Thickening agent(s) | 0.80 | 0.80 |
| Perservative(s) | 0.45 | 0.45 |

The composition of formula A had a pH of 6.6 while the composition of formula B had a pH of 6.7.

In order to determine whether compositions containing oat extract according to the present invention were therapeutically effective in enhancing the natural rate of skin desquamation the following test was conducted. The compositions of Table 1 were prepared. A control composition was prepared containing the ingredients as set forth in Table 2, below.

TABLE 2

| Ingredient | Control (wt. %) |
|---|---|
| Ethanol | 20.00 |
| Lactic acid | 5.00 |
| DI Water | Q.S. |
| Sodium Hydroxide | To pH 3 |

The material is applied and the increase in skin cell renewal (exfoliation) rate was measured according to the dansyl chloride procedure described and referred to in Soap/Cosmetics/Chemical Specialties for September 1993 at pp. 54–58 and 76.

The material is applied to the nasal fold area and stinging is subjectively assessed on a 4-point scale. A stinging evaluation is made at 0, 1, 2, 3, 4, 5, 7, 10, 12, and 15 minutes after the material is applied. The total sting score is summed. A maximum score could therefore be 40 while the minimum score could be 0. In general, products with a total score of 20 or more are considered to be somewhat irritating. The greater the Therapeutic Index, the more desirable the product.

The Therapeutic Index is calculated using the following formula:

TI=(percent increase in exfoliation/total sting score)×10

The results of a comparison of Formula A, B, and the Control are set forth in Table 3.

TABLE 3

| Formula | Exfoliation (% increase) | Stinging | TI |
|---|---|---|---|
| A | 17.2 | 10.1 | 17.0 |
| B | 20.2 | 8.9 | 22.7 |
| Control | 30.6 | 22.6 | 13.5 |

The results show that the presence of the oat extract surprisingly and unexpectedly increased cell renewal rate while maintaining or reducing irritation to levels substantially below that of known cell renewal actives.

EXAMPLE 2

The following compositions were prepared:

| Ingredient | 1 (wt %) | 2 (wt %) | 3 (wt %) | 4 (wt %) | 5 (wt %) | 6 (wt %) |
|---|---|---|---|---|---|---|
| D.I. Water | 69.94 | 83.24 | 78.24 | 78.24 | 93.75 | 88.75 |
| Glycerin | 4.00 | 4.00 | 4.00 | 4.00 | 0.00 | 0.00 |
| Butylene Glycol | 3.00 | 3.00 | 3.00 | 3.00 | 0.00 | 0.00 |
| Hydroxyethylcellulose Gum | 0.40 | 0.40 | 0.40 | 0.40 | 0.40 | 0.40 |
| Xanthan Gum | 0.40 | 0.40 | 0.40 | 0.40 | 0.40 | 0.40 |
| Methylparaben | 0.15 | 0.15 | 0.15 | 0.15 | 0.15 | 0.15 |
| Combination of Lactic Acid/Citric Acid/Malic Acid (from Green Tea Extract, lactic acid, and Acerola cherry fermentate) (48% active) | 10.5 | 0.00 | 0.00 | 0.00 | 0.00 | 0.00 |
| NaOH (50%) | 1.80 | 0.00 | 0.00 | 0.00 | 0.00 | 0.00 |
| PEG-20 (Polyethylene Glycol) | 5.00 | 5.00 | 5.00 | 5.00 | 0.00 | 0.00 |
| Panthenol | 0.50 | 0.50 | 0.50 | 0.50 | 0.00 | 0.00 |
| Proline | 0.05 | 0.05 | 0.05 | 0.05 | 0.00 | 0.00 |
| PCA (Pyrrolidone Carboxylic Acid) | 0.05 | 0.05 | 0.05 | 0.05 | 0.00 | 0.00 |
| Sodium PCA | 2.00 | 2.00 | 2.00 | 2.00 | 0.00 | 0.00 |
| Algae Extract | 0.10 | 0.10 | 0.10 | 0.10 | 0.00 | 0.00 |
| Kola Nut/Guarana/Mate Extracts | 0.50 | 0.50 | 0.50 | 0.50 | 0.00 | 0.00 |
| Sodium Hyaluronate (0.5% Solution) | 0.20 | 0.20 | 0.20 | 0.20 | 0.00 | 0.00 |
| Oat Extract (Canamino) | 1.00 | 0.00 | 5.00 | 0.00 | 0.00 | 0.00 |
| Oat Extract (Brooks) | 0.00 | 0.00 | 0.00 | 5.00 | 5.00 | 10.00 |
| Saccharide Isomerate | 0.01 | 0.01 | 0.01 | 0.01 | 0.00 | 0.00 |
| Water/Glycerin/Phospholipids/Sphingolipids/Cholesterol | 0.10 | 0.10 | 0.10 | 0.10 | 0.00 | 0.00 |
| Phenonip (phenoxyethanol, methyl paraben, ethylparaben, propylparaben and butylparaben) | 0.30 | 0.30 | 0.30 | 0.30 | 0.30 | 0.30 |

The oat extract was obtained from either Canamino or Brooks, as noted in the table. Compositions 1–6 and a control having the formula set forth in Table 2 were tested according to the procedure described in Example 1. The results are set forth in Table 4.

TABLE 4

| Formula | Exfoliation (% increase) | Stinging | TI |
|---|---|---|---|
| 1 | 21.7 | 12.1 | 17.9 |
| 2 | 22.2 | 14.4 | 15.4 |
| 3 | 27.4 | 10.2 | 26.9 |
| 4 | 24.4 | 12.4 | 19.7 |
| 5 | 17.2 | 10.1 | 17.0 |
| 6 | 20.2 | 8.9 | 22.7 |
| Control | 30.6 | 22.6 | 13.5 |

The results show that the presence of the oat extract surprisingly and unexpectedly increased cell renewal rate while maintaining or reducing irritation to levels substantially below that of known cell renewal actives.

EXAMPLES 3

The following Table provides a range of compositions useful for daily application. The compositions have a pH of about 4.0.

TABLE 5

| Ingredient | (wt %) |
|---|---|
| Oat extract | 1–50 |
| Humectants | 5–30 |
| Skin conditioning agents | 0.001–30 |
| Thickeners | 0.1–5 |
| Preservatives | 0.01–2 |
| Water | Q.S. |

It should be understood that a wide range of changes and modifications could be made to the compositions and methods of this invention. It is therefore intended that the foregoing description illustrates rather than limits this invention, and that it is the following claims, including all equivalents, which define this invention.

What is claimed:

1. A method of enhancing the rate of mammalian skin exfoliation comprising topically applying to the skin a composition comprising an amount of oat extract effective to enhance the rate of mammalian skin exfoliation, where in the composition is completely free of hydroxy acid.

2. The method of claim 1 wherein the oat extract contains less than about 1% by weight β-glucan.

3. The method of claim 1 wherein the composition comprises a topically acceptable vehicle for topical application.

4. The method of claim 1 wherein the composition has a pH between about 5 and about 9.

5. The method of claim 1 wherein the oat extract contains from about 10% to about 90% by weight carbohydrate endogenous to oat extract and from about 10% to about 90% protein endogenous to oat extract.

6. The method of claim 1 wherein the composition is formulated as a solution, gel, lotion, cream or ointment.

7. The method of claim 1 wherein the composition is topically applied in an amount and for a period of time sufficient to enhance the rate the skin desquamation.

8. The method of claim 1 wherein the topical application is on at least a daily basis.

9. The method of claim 1 wherein the composition has a pH between 6.0 and 8.0.

10. The method of claim 1 wherein the composition comprises from about 0.05% by weight to about 30% by weight oat extract.

11. A method of enhancing the rate of mammalian skin exfoliation comprising topically applying to the skin a composition comprising from about 0.05% by weight to about 30% by weight of an oat extract that contains less than about 1% by weight β-glucan effective to enhance the rate of mammalian skin exfoliation and that contains from about 10% by weight to about 90% by weight carbohydrate and from about 10% by weight to about 90% by weight protein, wherein the composition has a pH between about 6.0 and about 8.0 where in the composition is completely free of hydroxy acids.

* * * * *